Figure 1:
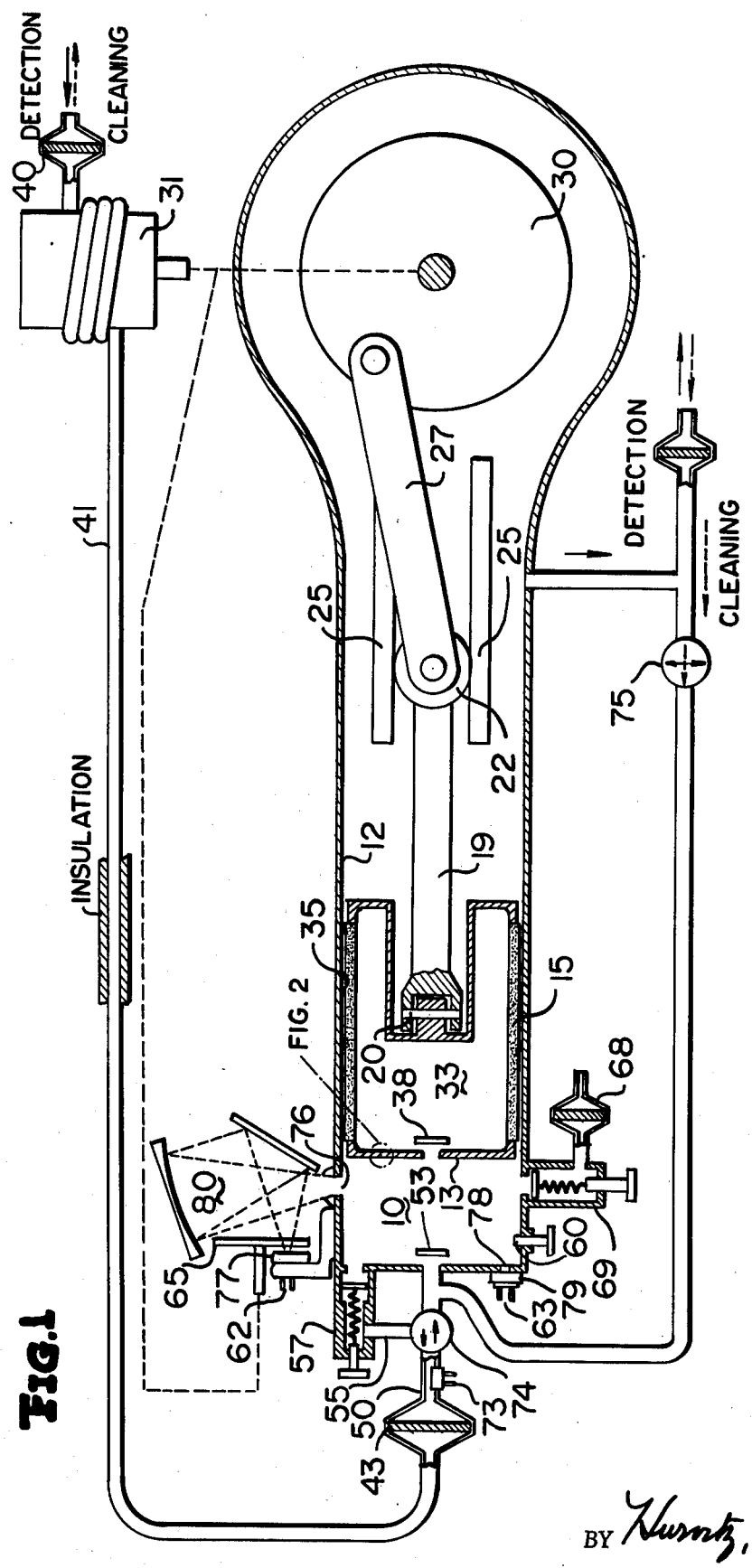

United States Patent [19]

Schuman

[11] 4,063,094

[45] Dec. 13, 1977

[54] GAS ANALYZER

[75] Inventor: Mark Schuman, Washington, D.C.

[73] Assignee: American Standard Inc., New York, N.Y.

[21] Appl. No.: 587,054

[22] Filed: Oct. 17, 1966

[51] Int. Cl.$^2$ .............................................. G01J 1/00
[52] U.S. Cl. .................................. 250/338; 250/336; 250/339; 250/343; 250/345; 356/81; 356/85
[58] Field of Search ................. 250/83.3 IR, 361, 343, 250/344, 345, 338, 339, 337, 336; 73/25, 26; 356/81, 85

[56] References Cited

U.S. PATENT DOCUMENTS 3,005,097  10/1961  Hummel .................. 250/83.3 IR

Primary Examiner—S. C. Buczinski

[57] ABSTRACT

Presence of a substance in a gaseous medium is detected by introducing a sample of the gaseous medium under consideration into a variable volume cavity formed by the walls of a cylinder and the operating face of a piston reciprocable in the cylinder, the adiabatically compressing the gas in the cavity by cyclic reciprocation of the piston to increase the temperature of the gas and thereby cause emission of radiant energy by constituents of the gas sample at their respective characteristic emission spectra. The emissions are modulated in accordance with the recurrent variation of volume of the cavity. The piston is gas-centered during operation to inhibit sliding contact between surfaces and thereby permit oilless and powderless operation which would otherwise present contaminants tending to interfere with detection of the substances of interest. A portion of the wall of the cavity has a multi-layer composition that cancels greybody signals resulting from movement of the piston and presence of interfering substances, and initial calibration is achieved by insertion into the cavity of a material whose emission spectrum is known in advance.

10 Claims, 2 Drawing Figures

U.S. Patent

Dec. 13, 1977

4,063,094

INVENTOR
MARK SCHUMAN

BY Hurvitz, Rose & Greene

ATTORNEYS

GAS ANALYZER

The present invention relates generally to gas analyzers, and more particularly to apparatus for detecting the presence of chemical vapors in gases and for measuring the concentration of such chemical vapors.

In my co-pending application for U.S. Letters Patent, Ser. No. 462,380, filed June 8, 1965, and entitled "Adiabatic Compression Infrared Emission Vapor Detector", I describe apparatus and methods for detecting and measuring trace amounts of chemical substances, such as vapors, agents, or aerosols, which may be present in a gaseous medium. Briefly, the apparatus there disclosed comprises a variable-volume optical absorption cell in the form of a cylinder, chamber or cavity having optically polished surfaces for enhancing the reflection of radiant energy therefrom in random optical paths, an intake valve for introducing a sample of the gas to be analyzed into the cavity, an exhaust valve for removing for use a variable quantity of compressed gas from the cavity, means for periodically varying the volume of the cavity to modulate the pressure and temperature of the confined gas in an adiabetic cycle and thus to produce modulated spectral radiance at the characteristic emission wavelengths of the gaseous medium and any foreign substances therein, the last-named means also providing, in conjunction with the intake and exhaust valves, for replacement of a fraction of the gas sample under observation with a fresh sample during each cycle of the periodic volume variation of the cavity, and monitoring and/or measuring apparatus for detecting the presence and/or concentration of the substance in question by observation of infrared emissions at the characteristic wavelengths of that substance. A brief treatment of the theory underlying the invention is also contained in the co-pending application.

In essence, the theory establishes that a highly reflective compression chamber in which a gaseous medium is subjected to periodic and approximately adiabatic compression and expansion, serves as a randomized optical chamber or cavity. The periodic temperature, gas concentration, and geometry variation produces a spectral infrared radiance variation in the cavity which may be monitored by infrared detectors, either on the chamber wall or external to the chamber, using either fixed or optically scanning infrared filters. The detectors can be tuned to the frequency and phase of the piston using synchronous rectification.

That theory is also applicable to the present invention which relates to improvements in the apparatus of my preceding invention and in added features thereto. A feature of the present invention is the use, in the apparatus briefly described above, of a gas centered piston as a portion of the means for periodically varying the volume of the cavity. Such an arrangement eliminates sliding surfaces, except during starting, stopping, or extreme vibration, and thus achieves low wear, long life and oilless and essentially powderless operation of the moving parts of the variable-volume chamber.

A further feature of the present invention resides in the provision of means for approximately cancelling the greybody signal accompanying the chopping of the cylinder (chamber) wall by the piston and greybody effects caused by the interfering chemicals or particulates. This feature provides automatic tracking of the responsivities of a pair of detectors, in order to reduce drifts and greybody interferences.

Another feature of the invention lies in the provision of means for filtering dust and other relatively large particles from the gas sample introduced into the chamber, and means for automatically cleaning the dust filter means by reversing the flow at pressures up to nearly the peak chamber pressure, thereby ejecting conglomerated dust and foreign bodies from the intake.

Still another feature of the present invention is the provision of means for calibrating the detection apparatus, preferably in the form of a thin piece of spectral material adjustably insertable into the optical compression chamber, to obtain quantitative measurements of the concentrations of substances in the gas sample under observation.

Apparatus in accordance with the present invention is useful in a variety of applications; for example, as an air pollution monitor, a leak detector in chemical processing or handling facilities, and in the detection of chemical warfare agents, or of toxic components of rocket fuels.

As will subsequently be more fully described, the apparatus of the invention may be modified to operate as an oilless pressure/vacuum pump, or may be used simultaneously or alternatively as a gas analyzer and/or a pump.

Accordingly, it is a principal object of the present invention to provide apparatus for the analysis of samples of a gaseous medium for determining the presence and/or concentration of contaminants therein by examining the periodic infrared spectral emissions therefrom as the gas sample is subjected to periodic adiabatic compression.

Another object of the invention is to provide apparatus suitable for use as an oilless pump.

Advantages of the invention over prior art gas analyzers, concentration monitors, and pumps include increased sensitivity, reliability, ruggedness, low power consumption, economy of operation, low wear, multichemical monitoring capability, and increase in the servicing interval.

Figure 2:
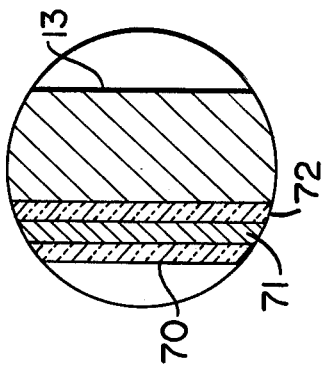

The above and still further objects, features and attendant advantages of the present invention will become apparent from a consideration of the following detailed description of certain preferred embodiments thereof, especially when taken in conjunction with the accompanying drawing, in which:

FIG. 1 is a sectional view of a preferred embodiment of the compression chamber and associated apparatus of the invention; and FIG. 2 is a sectional view of a fragmented portion of the wall of the compression chamber of FIG. 1.

Referring now to the drawings, the system of FIG. 1 includes a compression chamber 10 comprising a cavity formed by the walls of a cylinder 12 and the operating face 13 of a piston 15. Cylinder 12 and the wall forming the operating face 13 of piston 15 are preferably shaped in such manner that at maximum compression, i.e., at the top of the piston stroke, the cavity or chamber 10 formed by those elements possesses a large volume-to-surface area ratio, in order to minimize thermal loss to and optical loss at the wall surfaces. The desired large volume-to-surface area ratio exists in such geometrical shapes as a sphere, or a cylinder having a length equal to its diameter. The latter configuration is readily achieved in the structural shape of the cylinder and the top face of the piston as shown in the embodiment of FIG. 1. Alternatively, a spherical shape may be provided at maximum compression by utilizing a cylinder having a hemispherical end wall and a piston having a hollowed-out hemispherical top or operating face.

Piston 15 is adapted to reciprocate within cylinder 12 under the force exerted thereon by a piston rod 19, coupled at one end to the piston by a ball-and-socket or a universal joint 20, and at the other end to a conventional crosshead 22 with ball bearings. Crosshead 22 rolls on the bearings with relatively low friction within guide rails 25 and is driven by a connecting rod 27 pivotally fastened to both the crosshead and a crank 30 driven by motor 31.

Piston 15 is hollow, having a chamber 33 therein, and has a smaller outer diameter than the inner diameter of cylinder 12 so that when its axis is coincident with the cylinder axis an annular gap 35 is present between the two cooperating members. The piston walls are preferably composed of a material of sufficiently high porosity to permit escape of gaseous matter therethrough. Sintered bronze is an example of a suitable material. Alternatively, piston 15 may be provided with a ring or rings of exhaust ports (not shown) communicating with chamber 33 and gap 35. In either event, the piston has associated therewith a check valve 38 by which compressed gas from cavity 10 enters and is stored within chamber 33.

The inlet system for introducing samples of the gaseous medium under observation into compression chamber 10 of cylinder 12 includes a coarse filter 40 separated by an insulated duct 41 from a fine filter 43. The coarse filter preferably comprises a mesh screen for blocking the passage of relatively large dust particles or other particulate matter so as to prevent clogging of the fine filter thereby. The intake duct and therefore the intake air is warmed by the motor to enhance the infrared signal by raising intake gas temperature and to insure evaporation of large aerosol droplets which may be deposited in the intake components. The gas intake or inlet system further includes a tube or port 50 coupling duct 41 to the compression chamber 10 via an intake check valve 53. A second tube or port 55 between duct 50 and chamber 10 includes a spring-loaded regulating valve 57 and acts as a by-pass to permit a regulatable amount of gas under pressure to be forced out of the chamber 10 during compression such such that any blocking or conglomerate particles are blown free of filters 43 and 40. This operation is triggered by a vacuum sensor 73 which detects the partial vacuum existing at the bottom of the stroke (i.e., piston operated to the right as viewed in the Figure) when either filter becomes clogged. A partial vacuum occurs under such conditions as a result of piston 15 attempting to draw air through the clogged filters. The sensing of this partial vacuum is utilized to switch valves 74 and 75 to their respective cleaning positions in which the air flow is reversed for a predetermined period of time encompassing several strokes of the piston.

A calibrator 60 for the analyzer, in the form of a thin piece of spectral material, such as polystyrene, for example, is adjustably inserted within chamber 10 such that the length of spectral material exposed within the chamber may be varied. A pair of infrared detectors 62, 63, such as bolometers, are utilized for reducing drifts caused by the variable greybody signal resulting from the chopping of the cylinder wall by the piston, detector 62 having a filter wheel 65 which may be driven by the motor 31 and geared down to facilitate scanning of the characteristic emission wave lengths of the substance or substances under observation. A high pressure outlet 68 and spring-loaded valve 69 are also provided, for exhausting compressed gas from the chamber 10.

The wall surfaces forming the compression chamber are rendered highly reflective by conventional optical polishing techniques so as to reflect incident radiant energy, resulting from spectral emissions, along random paths within the chamber.

In operation of the system of FIG. 1, a sample of air or other gaseous medium is introduced into compression chamber or cavity 10 during cyclic withdrawal of piston 15 (that is, during the cylinder expansion stroke) via the above-described gas intake system. During introduction of the sample, the heavier particulates may tend to clog the coarse filter 40 while finer particulate matter may conglomerate on fine filter 43. When either of these conditions becomes severe the cleaning period is initiated by the vacuum sensor 73 and the filter clogging particles are blown or washed free of the respective filter by the gas forced from the compression chamber via the by-pass tube 55 and regulating valve 57. This operation takes place during a small portion of the cycle beginning at that time when the pressure in the chamber is sufficient to overcome the spring tension of valve 57. I have found that pressures up to approximately 5 gauge atmospheres with a four-to-one compression ratio may be developed in the compression chamber and are adequate to produce the desired automatic cleaning of the filter system during operation. The blocking particles dislodged from the filter during this sequence of events are ejected from the intake.

Initially, that is, during the first few cycles after starting of the driving means for piston 15, the piston will be in sliding contact with the inner surface of cylinder 12 until a sufficient quantity of the introduced gas enters the chamber 33 therein, via a check valve 38. Continuous leaking of this stored gas, under high pressure, through the porous wall of the piston forces the piston to assume a position in which its axis is substantially coincident with the axis of cylinder 12. Thus the piston is gas centered during operation, the universal joint or ball-and-socket arrangement 20 permitting angular orientation of the piston by the gas during operation. The volume of the hollow piston should be on the order of 20 percent of the volume of compression chamber 10 at maximum compression in order to maintain sufficient pressure in chamber 33, throughout the stroke, to center the piston. The porosity of the material of which the longitudinal piston wall is composed presents an infinite number of leakage holes to the gas stored in chamber 33. This results in greater efficiency and reliability than is attainable using one or more rings of exhaust ports on the piston wall.

The annular gap 35 between piston and cylinder surfaces is small, preferably on the order of 0.0005 inch when the piston axis is aligned with the cylinder axis. Hence, while gas will leak from the compression chamber via the space about the piston, the total leakage per stroke is only a small fraction of the gas within the compression chamber and is practically negligible when the apparatus is employed for gas analysis. The gas flow around the piston does not admit of the production of a high vacuum, but the unit does have a good partial vacuum capability, in the event that it is to be utilized as a vacuum pump.

As the air or other gas introduced to chamber 10 undergoes substantially adiabatic periodic compression under the cyclic reciprocation of piston 15, the pressure of the gas sample varies as $TV^{\gamma-1} = K$ (or $PV^\gamma = K'$) where $T$ is the temperature, $V$ is the volume, and $\gamma$ the ratio of specific heats at constant pressure and constant volume of the gas sample, and $K$ and $K'$ are constants. This increase in temperature of the gas sample accompanying the pressure modulation thereof results in the emission of radiant energy from the constituents of the sample at their respective characteristic infrared wavelengths. Spectral filter wheel 65 is selected to permit passage of radiant energy, reflected in random paths from the walls of chamber 10, of the wavelengths of interest. Hence, some of this emitted energy is incident on the chamber window 76 and is focused by a conventional optical system 80 on the detector 62. A fixed filter 77 is preferably used to block out radiant energy outside the wavelength region scanned by filter wheel 65. Detector 63 receives radiant energy from chamber 10 via an optical window 78 and fixed blocking filter 79. A suitable detector is a thermistor bolometer which may be connected in a bridge circuit with the detector 63, followed by a synchronous rectifier, logic network for wavelength selection and addition, and a contaminant concentration meter or a qualitative monitoring device, such as an alarm. The meter or alarm are, of course, utilized to indicate the amount and/or presence of an excessive quantity of the chemical agent or vapor of interest in the gaseous medium. It is obviously desirable that advance information be given to the system operator as to the type of chemical substance of contaminant to be detected so that the spectral filter wheel may be designed accordingly. Appropriate design facilitates detection of several possible contaminants by appropriate scanning of different bands of the emission spectrum by the filter. If only a single analytical and a single reference band are to be monitored the scanning filter is unnecessary, and both detectors could simply utilize fixed filters along with the optics shown in conjunction with detector 62.

Reciprocation of piston 15 (i.e., "chopping" of the cylinder wall) results in the existence of a phase-related greybody signal which may affect the d.c. signal obtained by synchronous rectification of the detector bridge output, and hence produce an error in the measure of gas spectral characteristics. To cancel or substantially eliminate this cylinder chopping signal, a portion of the wall of chamber 10, other than that traversed by the piston, is provided with a three-layer sandwich as shown more clearly in FIG. 2. Specifically, the face 13 of piston 15 and the end wall of the cylinder (if desired), may be covered with coextensive contiguous layers of transparent thermal insulator 70, metal 71, and thermal insulator 72. The layer 70 should be chemically inert with respect to the gas or gases to be analyzed, and should be a good thermal insulator. It may alternatively be composed of a dielectric or semi-conductive material, such as germanium, zinc sulfide, or zinc selenide, for example. Obviously, layer 70 should not be composed of any material which absorbs infrared radiation. The metal layer 71 is composed of a metal having good reflectivity such as aluminum, gold, copper or silver. Layer 72 need not be transparent but may otherwise be identical to layer 70. The thicknesses of the three layers and perhaps the emissivity of the metal layer are selected to adjust the magnitude and phase of the greybody signal emitted by the metal layer as it follows (but lags) the gas temperature variation, to produce a component that approximately cancels the cylinder chopping in-phase greybody signal. The desired thicknesses of the layers also depend upon the specific heat and thermal conductivity of the layers; thicknesses on the order of 0.001 - 0.0001 - 0.001 inch are representative for layers 70, 71, and 72, respectively. The out-of-phase component of the emitted signal which lags the phase of the piston cycle by 90 electrical degrees provides a sufficient greybody signal to equalize the responsivities of the two detectors. Emission by layer 70 can be made negligible by proper choice of material.

The magnitude and polarity of the d.c. signal obtained by the synchronous rectification of the out-of-phase greybody signal is indicative of the magnitude and polarity of the responsivity difference of the two detectors, the slope of the blackbody curve at wall temperature, and optical transmission. This d.c. output signal may be used to provide automatic tracking of the responsivity of one detector by that of the other for the particular greybody signal, such as by varying the relative bias of the two detectors to cancel any difference in response. The in-phase rectified output signal is then a true measure of the spectral characteristics of the constituents of the gaseous medium under observation, and is essentially independent of in-phase greybody signal caused by either incomplete cancellation of the cylinder chopping signal or, to a lesser extent, by greybody effects from interfering chemicals or particulates. The latter effects can be more completely eliminated by wavelength selection.

Initial calibration of the system is achieved by varying the degree of insertion of the spectral material (calibrator 60), having well-defined and known infrared lines, into the chamber, and comparing the resulting output signals with output signals resulting from known gas concentrations within the optical chamber. The calibrator may then be provided with suitable indicia of the comparison and thereafter used as a quantitative sensitivity check.

The high pressure outlet 68 with spring-loaded valve 69 may be eliminated if compressed gas is not desired, for example, in the event the unit is to be used only as a gas analyzer. The spring bias on valve 69 should otherwise be adjusted to permit opening of the valve only after there is sufficient pressure in the chamber for centering the piston. For pump operation, suction is available at the intake.

A number of variations are possible in the structure of the embodiment of FIG. 1. For example, a recirculating air flow system may be provided between and including filters 40 and 43, thereby subjecting the incoming gas to more heat from the motor to evaporate aerosols. Several detectors may be utilized at distinct windows in the chamber, in conjunction with optical transmission and wavelength selection apparatus, for multi-chemical monitoring.

For use solely as an oilless pressure/vacuum pump, the embodiment of FIG. 1 may be modified by eliminating the optical polishing of the compression chamber surfaces, and the calibrator and detector apparatus. Such features as the gas centered piston, the piston drive system, intake filters, and bypass valve for automatic filter cleaning, would be retained. Completely dust-free operation would be maintained by use of a filter, as shown, for the gas leaving pressure outlet 68.

While I have described and illustrated one specific embodiment of my invention, it will be clear that variation of the details of construction which are specifically illustrated and described may be resorted to without departing from the spirit and scope of the invention as defined in the appended claims.

I claim:

1. Apparatus for detecting the presence of chemical substances in a gaseous medium by detection of characteristic infrared spectral wavelengths of radiant energy emitted therefrom, said apparatus comprising a variable volume optical cavity; said optical cavity having highly reflective surfaces arranged to provide random optical paths for said emitted radiant energy; means for cyclically varying the volume of said cavity for adiabatic compression and expansion of a sample of said gaseous medium within said cavity, so that the temperature of said sample varies substantially as $TV^{\gamma-1} = K$, where $T$ is the temperature, $V$ the volume, and $\gamma$ the ratio of specific heat at constant pressure and specific heat at constant volume of said sample, and $K$ is a constant; and means for detecting radiant energy emitted at the characteristic infrared emission wavelength of the substance or substances sought to be detected, emanating from said sample as a result of said temperature variation; said optical cavity comprising a hollow cylinder having an end wall, said means for cyclically varying the cavity volume including a hollow gas centered piston reciprocable inwardly and outwardly of said cylinder and having a face in confronting relationship and forming with said end wall a cavity of high volume-to-surface area ratio at maximum compression of said sample.

2. The combination according to claim 1 wherein said cavity is cylindrical and has a length equal to its diameter at said maximum compression, to provide said high volume-to-surface area ratio.

3. The combination according to claim 1 wherein said hollow piston includes a check valve in the wall thereof communicating with said cavity for introducing a portion of the gas in said cavity into the chamber of said piston, and having a porous wall in confronting relationship with the cylindrical internal surface of said cylinder to provide high pressure outlets for the gas in said piston chamber for aligning the axis of said piston in substantial coincidence with the axis of said cylinder, the outer diameter of said piston being less than the inner diameter of said cylinder so that an annular gap is formed between said piston and said cylinder upon said alignment.

4. The combination according to claim 1 wherein said apparatus includes an intake system for introducing said sample into said cavity, said intake system including means for filtering particulate matter from the incoming sample, and a bypass valve communicating with said cavity and said filtering means to direct gas under pressure from said cavity onto said filtering means for cleaning conglomerated particulate matter therefrom.

5. The combination according to claim 1 further including means for cancelling the in-phase greybody signal accompanying reciprocation of said piston within said cylinder, said cancelling means comprising a multi-layer coating applied to at least a portion of the surfaces forming said cavity, the outer layer being transparent and the layer adjacent thereto being metallic, the layers having thickness selected to produce emission of a greybody signal by said metallic layer tending to cancel said in-phase greybody signal.

6. The combination according to claim 1 further including means for calibrating said detecting means for quantitative measurement of concentrations of said chemical substances in the samples under test, said calibrating means comprising a relatively thin piece of spectral material projecting into said cavity, and means for variably adjusting the amount of projection of said spectral material into said cavity.

7. The combination according to claim 3 wherein said piston chamber has a volume on the order of 20 percent of the volume of said cavity at maximum compression of said sample.

8. The combination according to claim 1 wherein said detecting means includes a pair of radiant energy detectors for receiving emissions from said cavity, and wherein is further included means for cancelling the in-phase greybody signal accompanying reciprocation of said piston within said cylinder, said cancelling means comprising a multi-layer coating applied to at least a portion of the surfaces forming said cavity, the outer layer being transparent and the layer adjacent thereto being metallic, the layers having thicknesses selected to produce emission of a greybody signal by said metallic layer, the last-named emission having a 90° out-of-phase component sufficient to equalize the responsivities of said two detectors to in-phase greybody signals.

9. Apparatus for detecting the presence and concentration of chemical substances in a gaseous medium by observation of characteristic infrared spectral wavelengths of radiant energy emitted therefrom, said apparatus comprising a variable volume optical cavity having highly reflective surfaces arranged to provide random optical paths for said emitted radiant energy, said cavity comprising a hollow cylinder having an end wall, and further including means for reducing greybody signal accompanying variation of the volume of said cylinder, means for introducing a sample of said gaseous medium into said cavity, a hollow piston reciprocable within said cylinder to cyclically vary the volume of said cavity, for substantially adiabatic compression and expansion of said sample so that increase in temperature of said sample during compression thereof to produce radiant energy emissions from constituents thereof is a function of the decrease in volume of said cavity, said piston containing a chamber having a gas-pervious cylindrical wall adjacent the cylindrical surface of said cylinder, a check valve in said piston to permit introduction of a portion of the gaseous sample in said cylinder into said piston chamber during the compression stroke of said piston, whereby controlled leakage of the portion of said sample in the chamber through the gas-pervious wall thereof produces gas centering of said piston relative to said cylinder during reciprocation, and means responsive to radiant energy emitted at the characteristic infrared emission spectrum of the substance of interest for detecting said presence thereof.

10. The invention according to claim 9 further including means in said cavity for calibrating said detecting means to permit quantitative measurement of concentration of said substance of interest in the sample under test.

* * * * *